US00PP15315P2

(12) United States Plant Patent
Hendarto

(10) Patent No.: US PP15,315 P2
(45) Date of Patent: Nov. 16, 2004

(54) ***NEPHROLEPIS* FERN PLANT NAMED 'TIGER FERN'**

(50) Latin Name: *Nephrolepis exaltata*
Varietal Denomination: Tiger Fern

(75) Inventor: Chandra Gunawan Hendarto, Bogor (ID)

(73) Assignee: Exotic Foliage Nursery, Inc, Miami, FL (US)

( * ) Notice: Subject to any disclaimer, the term of this patent is extended or adjusted under 35 U.S.C. 154(b) by 0 days.

(21) Appl. No.: 10/753,805

(22) Filed: Jan. 8, 2004

(51) Int. Cl.[7] ..... A01H 9/00
(52) U.S. Cl. ..... Plt./379
(58) Field of Search ..... Plt./379

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Nephrolepis* Fern plant named 'Tiger Fern', characterized by its upright and outwardly arching plant habit; vigorous growth habit; durable rachis; green and yellow green variegated pinnae; and closely-spaced pinnae; densely foliated.

2 Drawing Sheets

Botanical classification/cultivar designation: *Nephrolepis exaltata* cultivar Tiger Fern.

BACKGROUND OF THE INVENTION

The present invention relates to a new and distinct cultivar of *Nephrolepis* Fern plant, botanically known as *Nephrolepis exaltata*, and hereinafter referred to by the name 'Tiger Fern'.

The new *Nephrolepis* fern was discovered by the Inventor in a controlled environment in Bogor, Indonesia in the spring of 2000, as a naturally-occurring whole plant mutation of an unnamed selection of *Nephrolepis exaltata*, not patented. The new *Nephrolepis* Fern was selected by the Inventor on the basis of its unique pinnae variegation.

Since 2000, asexual reproduction by divisions of the new cultivar in a controlled environment in Bogor, Indonesia, has shown that the unique features of this new *Nephrolepis* Fern are stable and retained through more than 30 successive generations of asexual reproduction.

SUMMARY OF THE INVENTION

The following traits have been repeatedly observed and are determined to be the unique characteristics of 'Tiger Fern'. These characteristics in combination distinguish 'Tiger Fern' as a new and distinct cultivar of *Nephrolepis* Fern:

1. Upright and outwardly arching plant habit.
2. Vigorous growth habit.
3. Durable rachis; plants resist breakage during shipping.
4. Green and yellow green variegated pinnae.
5. Closely-spaced pinnae; densely foliated.

The new *Nephrolepis* Fern is most similar to the parent, the unnamed selection of *Nephrolepis exaltata*. However in side-by-side comparisons conducted in Bogor, Indonesia and Miami, Fla., plants of the new *Nephrolepis* Fern differ from the parent selection primarily in pinnae coloration as plants of the parent selection have solid green-colored pinnae.

BRIEF DESCRIPTION OF THE PHOTOGRAPHS

The accompanying colored photographs illustrate the overall appearance of the new *Nephrolepis* Fern cultivar, showing the colors as true as it is reasonably possible to obtain in colored reproductions of this type. Colors in the photograph may differ slightly from the color values cited in the detailed botanical description which accurately describe the colors of the new *Nephrolepis* Fern.

The photograph on the first sheet comprises a side perspective view of a typical hanging basket plant of 'Tiger Fern'.

The photograph on the second sheet comprises a close-up view of a typical frond of 'Tiger Fern'.

DETAILED BOTANICAL DESCRIPTION

The cultivar Tiger Fern has not been observed under all possible environmental conditions. The phenotype may vary somewhat with variations in environment such as temperature and light intensity without, however, any variance in genotype. The aforementioned photographs and following observations and measurements describe plants grown in Miami, Fla., under commercial practice in a shaded polyethylene-covered greenhouse. During the production of the plants, day temperatures ranged from 18 to 30° C. and night temperatures ranged from 2 to 15° C. Rooted young plants were planted in 25-cm hanging basket containers and were about four months old when the photographs and the description were taken. In the following description, color references are made to The Royal Horticultural Society Colour Chart, 1995 Edition, except where general terms of ordinary dictionary significance are used.

Botanical classification: *Nephrolepis exaltata* cultivar Tiger Fern.

Parentage: Naturally-occurring whole mutation of an unnamed selection of *Nephrolepis exaltata,* not patented.

Propagation:

*Type.*—By divisions.

*Time to initiate roots.*—Summer: About 10 days at 24° C. Winter: About 14 days at 18° C.

*Time to produce a rooted young plant.*—Summer: About 40 days at 24° C. Winter: About 60 days at 18° C.

*Root description.*—Fine; numerous.

Plant description:

*Plant/growth habit.*—Upright and outwardly arching; symmetrical; appropriate for 25-cm hanging baskets; vigorous; rapid growth rate.

*Plant height, soil level to top of plant plane.*—About 26 cm.

*Plant width.*—About 68 cm.

*Frond description.*—Leaf arrangement: One-pinnate. Frond length: About 47 cm. Frond width (widest point): About 15 cm. Rachis diameter: About 2.25 mm. Rachis strength: Strong, durable; rachis resist breakage during shipping. Rachis aspect: Outwardly arching. Rachis texture: Pubescent. Rachis color: Towards the apex, close to 146A; towards the base, close to 146A overlain with close to 183A.

*Pinnate description.*—Shape: Linear. Length: About 7.7 cm. Width: About 1.4 cm. Quantity of pinnae: Numerous, about 60 per frond. Margin: Finely crenate. Apex: Acute. Base: Truncate, asymmetrical. Aspect: Slightly reflexed. Surface: Undulate. Attachment: Sessile. Texture, upper and lower surfaces: Glabrous; smooth. Venation pattern: Pinnate. Color: Developing and fully expanded pinnae, upper surface: Alternating sectors of more green than 146A and close to 151A to close to 154A; sectors random and vary in shape and size. Developing and fully expanded pinnae, lower surface: Alternating sectors of close to 146B and more green than 151A to close to 154A; sectors random and vary in shape and size. Venation, upper and lower surfaces: Same as lamina.

*Spores.*—None observed.

Disease/pest resistance: Resistance to pathogens and pests common to *Nephrolepis exaltata* has not been observed on plants of the new *Nephrolepis* Fern.

Temperature tolerance: Plants of the new *Nephrolepis* Fern have been observed to tolerate temperatures from 1 to 32° C.

It is claimed:

1. A new and distinct cultivar of *Nephrolepis* Fern plant, named 'Tiger Fern', substantially as shown and described.

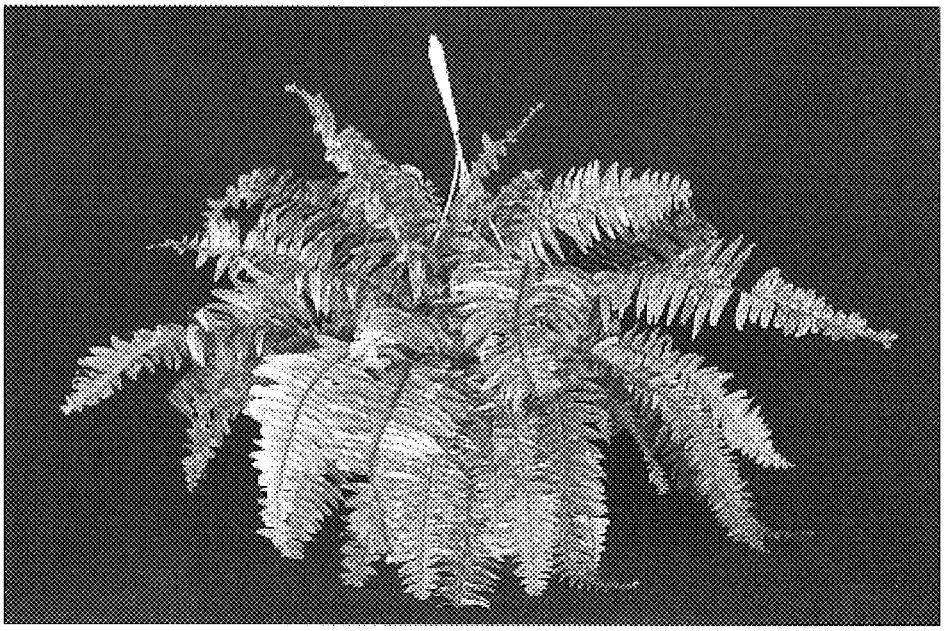

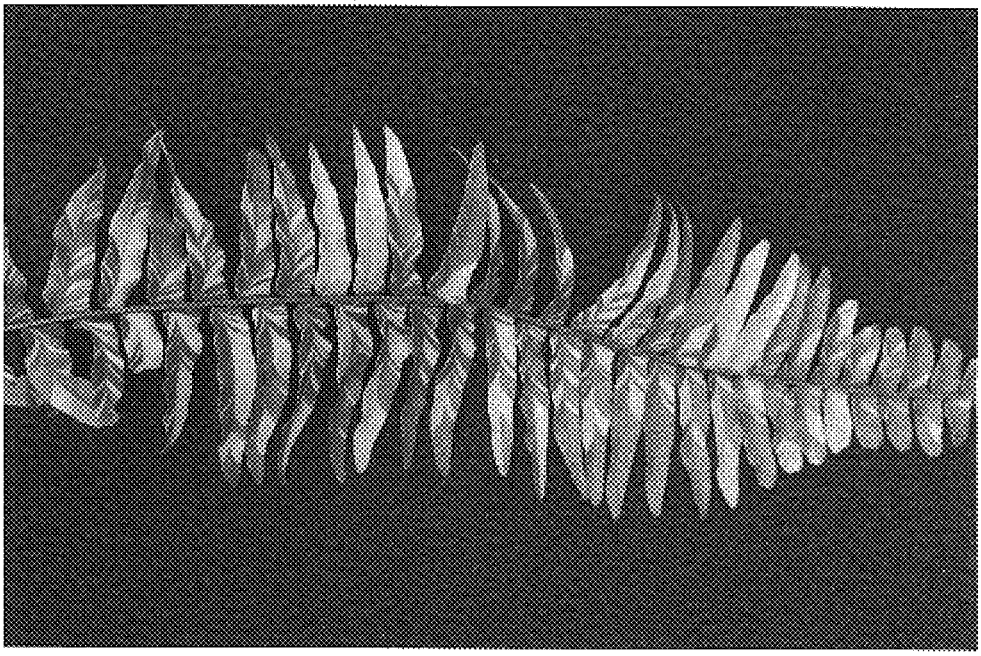

* * * * *